(12) United States Patent
Gliner et al.

(10) Patent No.: US 12,414,729 B2
(45) Date of Patent: Sep. 16, 2025

(54) FOCAL ARRHYTHMIA SOURCE FINDER USING DIRECTED GRAPHS

(71) Applicant: BIOSENSE WEBSTER (ISRAEL) LTD., Yokneam (IL)

(72) Inventors: Vadim Gliner, Haifa (IL); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 401 days.

(21) Appl. No.: 17/991,953

(22) Filed: Nov. 22, 2022

(65) Prior Publication Data

US 2024/0164693 A1 May 23, 2024

(51) Int. Cl.
*A61B 5/367* (2021.01)
*A61B 5/341* (2021.01)
*A61B 5/364* (2021.01)
*A61B 5/283* (2021.01)

(52) U.S. Cl.
CPC .............. *A61B 5/364* (2021.01); *A61B 5/341* (2021.01); *A61B 5/367* (2021.01); *A61B 5/283* (2021.01)

(58) Field of Classification Search
CPC .......... A61B 5/367; A61B 5/339; A61B 5/341
See application file for complete search history.

(56) References Cited

U.S. PATENT DOCUMENTS

| | | |
|---|---|---|
| 5,391,199 A | 2/1995 | Ben Haim |
| 5,443,489 A | 8/1995 | Ben Haim |
| 5,558,091 A | 9/1996 | Acker |
| 6,172,499 B1 | 1/2001 | Ashe |
| 6,239,724 B1 | 5/2001 | Doron |
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben Haim |
| 6,788,967 B2 | 9/2004 | Ben Haim |
| 6,892,091 B1 | 5/2005 | Ben Haim |
| 7,536,218 B2 | 5/2009 | Govari |
| 7,756,576 B2 | 7/2010 | Levin |
| 7,848,787 B2 | 12/2010 | Osadchy |
| 7,869,865 B2 | 1/2011 | Govari |
| 8,456,182 B2 | 6/2013 | Bar-Tal |
| 2020/0273170 A1 | 8/2020 | Blake, III |
| 2020/0367751 A1* | 11/2020 | Vandersickel ......... A61B 5/316 |

(Continued)

OTHER PUBLICATIONS

International Search Report for corresponding PCT Appln. No. PCT/IB2023/061542 dated Mar. 4, 2024.

(Continued)

*Primary Examiner* — George R Evanisko
(74) *Attorney, Agent, or Firm* — Volpe Koenig

(57) ABSTRACT

A system includes a display and a processor. The processor is configured to (i) receive a cardiac electrophysiological (EP) velocity vectors map, (ii) compute a set of directed graphs from at least some of the velocity vectors, (iii) using the directed graphs, identify respective origin velocity vectors on the EP velocity vectors map, (iv) define one or more regions on the EP velocity vectors map, (v) determining based on origin velocity vectors in each of the one or more regions, whether the one or more regions contain a focal source of an arrhythmia, and (vi) visualize regions identified to contain a focal source on the EP map to a user, on the display.

17 Claims, 4 Drawing Sheets

(56) References Cited

U.S. PATENT DOCUMENTS

2020/0375489 A1 12/2020 Govari
2022/0015682 A1 1/2022 Spector

OTHER PUBLICATIONS

Vandersickel Nele et al: "Directed Networks as a Novel Way to Describe and Analyze Cardiac Excitation: Directed Graph Mapping", Frontiers in Physiology, vol. 10, Sep. 10, 2019 (Sep. 10, 2019), p. 1138.
Brooks DH et al: "Identification of Cardiac Rhythm Features by Mathematical Analysis of Vector Fields", IEEE Transactions on Biomedical Engineering, IEEE, USA, vol. 52, No. 1, Jan. 1, 2005 (Jan. 1, 2005), pp. 19-29.

* cited by examiner

US 12,414,729 B2

FOCAL ARRHYTHMIA SOURCE FINDER USING DIRECTED GRAPHS

FIELD OF THE DISCLOSURE

The present disclosure relates generally to cardiac electrophysiological (EP) mapping, and particularly to analysis of cardiac EP maps.

BACKGROUND OF THE DISCLOSURE

Computer aided analysis of EP maps that were generated from catheter-acquired EP signals was previously described in the patent literature. Such EP maps can aid in finding and planning treatment of arrhythmogenic tissue locations.

The present disclosure will be more fully understood from the following detailed description of the examples thereof, taken together with the drawings in which:

DETAILED DESCRIPTION OF EXAMPLES

Overview

Figure 1:
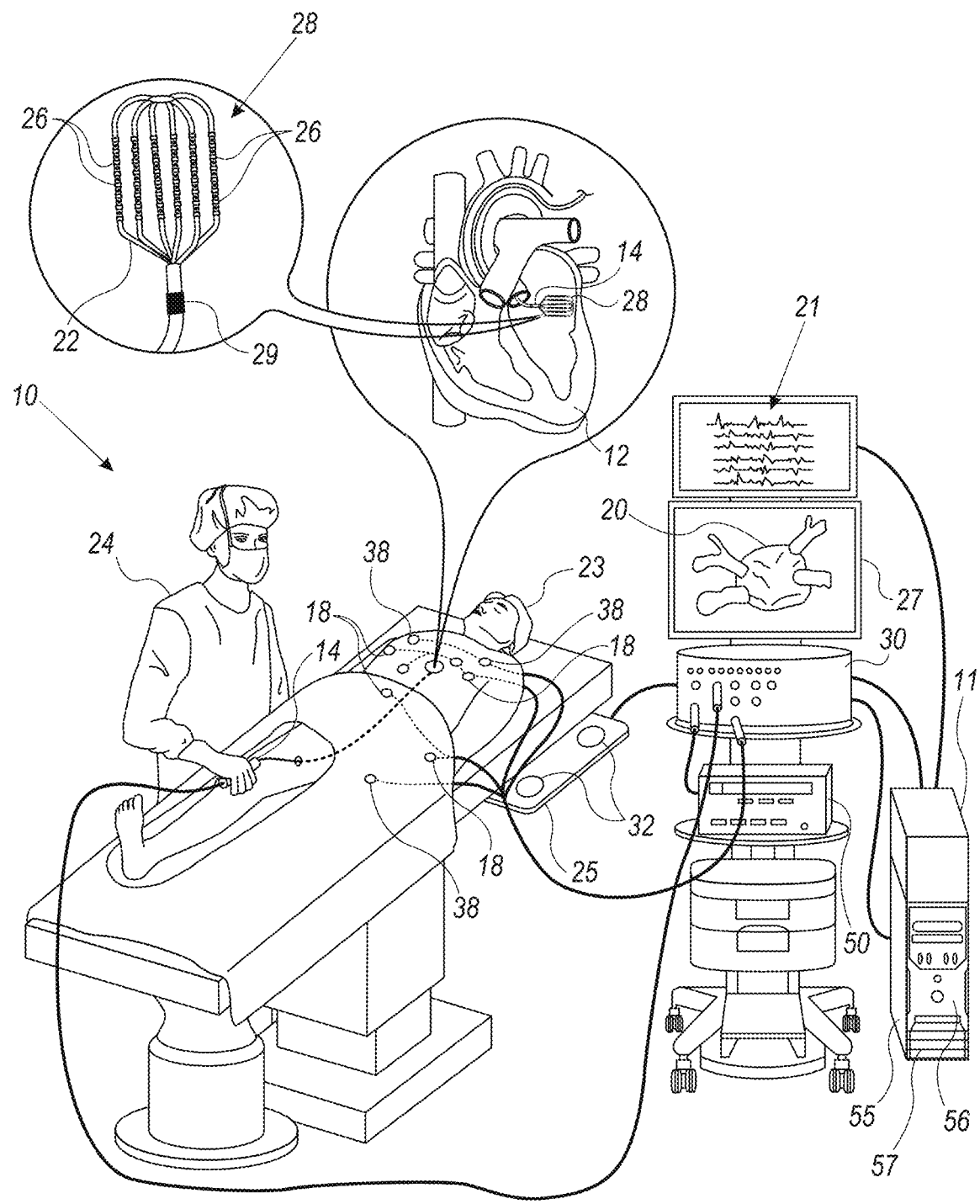
FIG. 1 is a schematic, pictorial illustration of a catheter-based electrophysiology (EP) mapping and ablation system, in accordance with an example of the present disclosure.

Probe-based (e.g., multi-electrode catheter-based) cardiac diagnostic and therapeutic systems may measure a large number of intra-cardiac electrophysiological (EP) signals, such as electrograms (EGM), during an invasive procedure. Typically, the analysis of such a vast amount of EP information is facilitated by generating and presenting one or more EP maps to a user (e.g., a physician or a clinical application specialist).

Various types of EP maps may be generated for an inner tissue surface of a chamber of a heart, such as a left atrium of a heart. One such map is sometimes called an activation wave propagation coherent map, also called hereinafter "velocity vectors map," in which vectors indicative of EP conduction velocities (speeds and directions) are overlaid on the cardiac anatomical surface.

A velocity vectors map may be used in attempting to detect a focal source causing an arrhythmia by visual inspection of the map. In some types of arrhythmias, however, such as in scar-related atrial tachycardias, the EP behavior has complex patterns, and an EP velocity vectors map displays visual clutter of multiple velocity vectors, making it difficult for a user to interpret. This poses a challenge for a physician performing an invasive catheterization session to diagnose and ablate one or more aberrant focal sources to eliminate an arrhythmia.

While computer-assisted analysis of EP conduction properties of a surface embedded in 3D space may further assist user inspections, such analysis is very difficult, and requires significant algorithmic and computational power. Furthermore, such an analysis may be incomplete, because, for example, full analysis of a manifold in 3D space requires more information than is available from the measured EP values.

Examples of the present disclosure that are described herein provide a method and an algorithm for automatically identifying a focal source of an arrhythmia. In some examples, a processor uses directed graphs to compute a relationship between velocity vectors. Based on the computed relationship, the processor identifies vector origins of the directed graphs. Using the directed graphs, the processor determines a subset of origin vectors of the velocity vectors. Then, the processor defines one or more regions on the EP velocity vectors map and identifies origin vectors that that are in spatial proximity to one another within each given region. The processor applies a divergence theorem to determine whether the identified origin velocity vectors that are in such proximity to one another behave in a way indicative of a focal source present in each relevant region.

In some examples, the processor generates or receives an EP map of velocity vectors {V}. The processor builds a set of directed graphs using a newly disclosed method in which the processor generates and aligns to each vector head a capturing volume in space, such as a cone with predefined radius and solid angle. If a tail of another vector falls within the capturing volume (e.g., cone), the processor generates from the two vectors a directed graph portion. The processor goes over all vectors, and deletes overlapping selectins (e.g., reoccurring directed graph portions), until a unique full set of directed graphs is received. Isolated vectors, e.g., that were not associated using the disclosed method with any other vectors are also considered (minimal) directed graphs.

Each arc in a directed graph has a defined direction, extending from a "tail" vertex to a "head" vertex. The processor analyzes each directed graph to identify arcs with their tails being the origins of an EP propagation. An origin arc is an arc in the directed graph that is only connected to arcs that extend away from the origin arc. There are no arcs that extend toward the origin arc.

The processor then strips each directed graph from its branches, which leaves only a set of "stripped" directed graphs, that are all origin arcs. At this stage the processor considers only vectors that correspond to the single origin arcs found, these vectors called hereinafter "origin vectors". The processor analyzes each such origin vector to identify tails of origin vectors that are in close proximity to one another. In one example, the processor defines a volume (e.g., an ellipsoid) that intersects an EP surface of and checks which tails (i.e., origin locations) on the surface can be enclosed within the ellipsoid.

In some examples, using a predefined criterion (e.g., minimal number of such vectors at each given volume), the processor fits a vector field function to the vectors (e.g., fits velocity vector field approximation function V(r)). In other examples the processor may consider the discrete set of origin vectors. However, fitting the function V(r) enhances the algorithm resilience to missing data (e.g., to incomplete mapping).

By applying the divergence theorem to V(r), the processor determines if the origin vectors all point away from a focal source. For example, if the vector derivative along each of the x, y, z axis is greater than 0, $\nabla \cdot V > 0$, the origin vectors are all pointing away from a focal source. In such case the processor will indicate the surface contained in the volume as containing a focal source of arrhythmia. In some examples, the processor may perform vector calculus analysis using either differential or integral analysis.

In one example, if the processor finds a location to be a focal point, the processor calculates an average location based upon tails of all vectors. Finally, the processor graphically indicates the identified cardiac tissue location on the EP map, e.g., a tissue area for a user to consider for ablation.

In some examples, the processor considers the entire set of directed graphs. In other examples, the processor considers (e.g., selects) a subset of directed graphs that are most unbalanced in favor of open-ended arcs. Considering a vertex of a graph, the number of head ends connected to (extending to) a vertex is called the indegree of the vertex. The number of tail ends connected to (extending from) a vertex is called its outdegree (also referred to as a branching factor in trees). The processor favors graphs having outdegree>indegree, and to this end may use a positive integer threshold that considers only directed graphs fulfilling (outdegree−indegree)≥N, N=1, 2, . . . . In another example, the processor considers only the simplest directed graphs, i.e., ones with only arcs branching from an origin. An example of such a simple directed graph is one with two vectors that are not parallel and originate from a same location, with the resulting direct graph possessing (outdegree−indegree)=2−0≥2.

System Description

FIG. 1 is a schematic, pictorial illustration of a catheter-based electrophysiology (EP) mapping and ablation system 10, in accordance with an example of the present disclosure.

System 10 may include multiple catheters, which are percutaneously inserted by physician 24 through the patient's vascular system into a chamber or vascular structure of a heart 12. In the shown example, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing intracardiac electrogram (IEGM) signals, catheters dedicated for ablation and/or catheters dedicated for both sensing and ablation. An example EP mapping catheter 14 that is configured for sensing IEGM is illustrated herein. Physician 24 brings a distal tip 28 (also called hereinafter "distal end assembly 28") of catheter 14 into contact with the heart wall for sensing a target site in heart 12. For ablation, physician 24 similarly brings a distal end of an ablation catheter to a target site for ablation.

Catheter 14 is an exemplary catheter that includes one, and preferably multiple, electrodes 26 optionally distributed over a plurality of splines 22 at distal tip 28 and configured to sense IEGM signals. Catheter 14 may additionally include a position sensor 29 embedded in or near distal tip 28 for tracking position and orientation of distal tip 28. Optionally, and preferably, position sensor 29 is a magnetic-based position sensor including three magnetic coils for sensing three-dimensional (3D) position and orientation.

Magnetic-based position sensor 29 may be operated together with a location pad 25 that includes a plurality of magnetic coils 32 configured to generate magnetic fields in a predefined working volume. Real-time position of distal tip 28 of catheter 14 may be tracked based on magnetic fields generated with location pad 25 and sensed by magnetic-based position sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on patient 23 to establish a location reference for location pad 25 as well as impedance-based tracking of electrodes 26. For impedance-based tracking, electrical current is directed toward electrodes 26 and sensed at electrode skin patches 38 so that the location of each electrode can be triangulated via electrode patches 38. Details of the impedance-based location tracking technology are described in U.S. Pat. Nos. 7,536,218; 7,756,576; 7,848, 787; 7,869,865; and 8,456,182.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more electrodes at a distal tip of a catheter configured for ablation. Energy produced by ablation energy generator 50 may include, but is not limited to, radiofrequency (RF) energy or pulsed-field ablation (PFA) energy, including monopolar or bipolar high-voltage DC pulses to be used to effect irreversible electroporation (IRE), or a combinations thereof.

Patient interface unit (PIU) 30 is an interface configured to establish electrical communication between catheters, electrophysiological equipment, power supply and a workstation 55 for controlling the operation of system 10. Electrophysiological equipment of system 10 may include, for example, multiple catheters, location pad 25, body surface ECG electrodes 18, electrode patches 38, ablation energy generator 50, and recorder 11. Optionally, and preferably, PIU 30 additionally includes processing capability for implementing real-time location computation of the catheters and for performing ECG calculations.

Workstation 55 includes memory 57, processor unit 56 with memory or storage with appropriate operating software loaded therein, and user interface capability. Workstation 55 may provide multiple functions, optionally including (1) modeling endocardial anatomy in three-dimensions (3D) and rendering the model or a POI map 20 for display on a display device 27, (2) displaying activation sequences (or other data) compiled from recorded electrograms 21 in representative visual indicia or imagery included in the rendered POI map 20 on display device 27, (3) displaying real-time location and orientation of multiple catheters within the heart chamber, and (4) displaying sites of interest, such as places where ablation energy has been applied, on display device 27. One commercial product embodying elements of system 10 is available as the CARTO™ 3 System, available from Biosense Webster, Inc., 31A Technology Drive, Irvine, CA 92618.

Focal Arrhythmia Source Finder Using Directed Graphs

Figure 2:
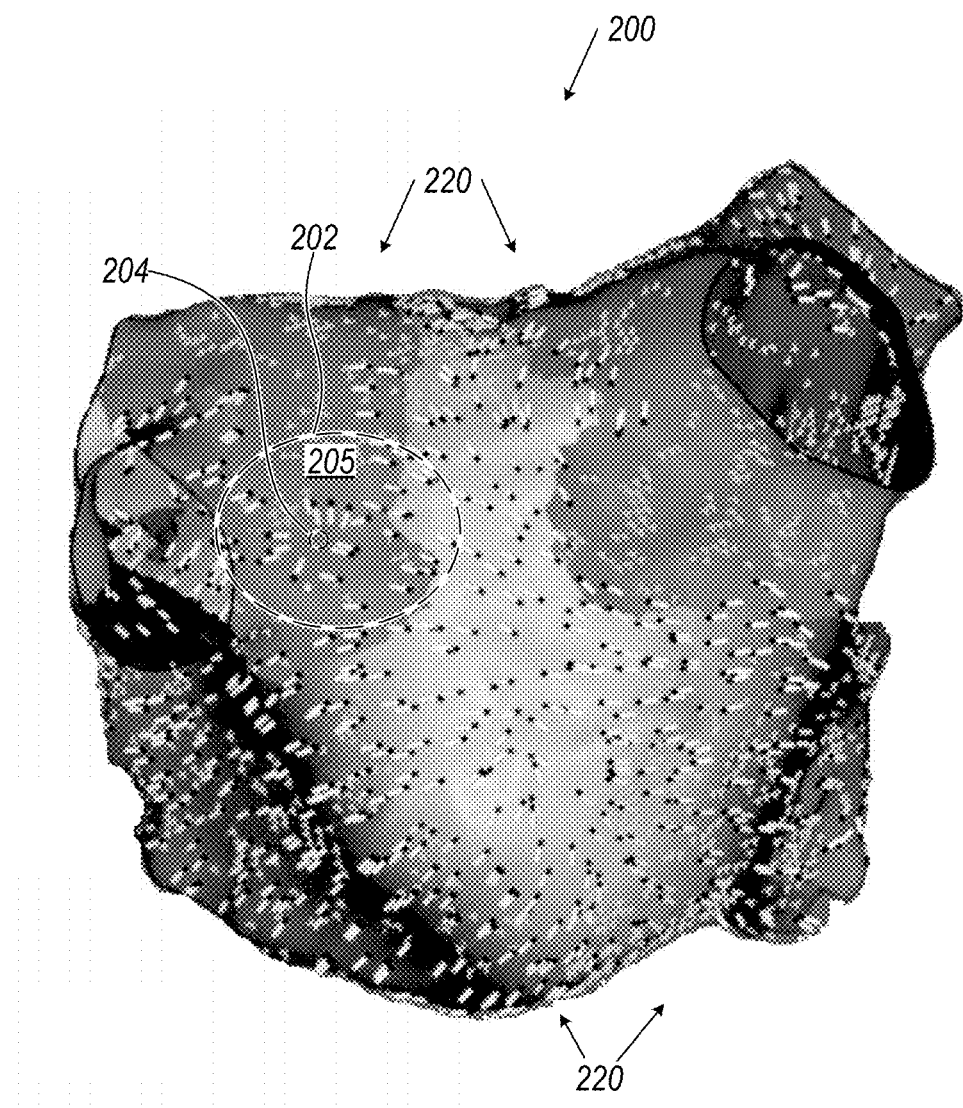
FIG. 2 is a schematic, pictorial volume rendering of a coherent EP activation map of a left atrium anatomy overlaid with conduction arrows that illustrate the propagation of the EP activation wave, in accordance with an example of the present disclosure.

FIG. 2 is a schematic, pictorial volume rendering of a coherent EP activation map 200 of a left atrium anatomy overlaid with conduction arrows 220 (also called herein "velocity vectors") that illustrate the propagation of an EP activation wave, in accordance with an example of the present disclosure.

Conduction arrows 220 are the aforementioned velocity EP vectors, all seen with a fixed length, and each with a direction of a respective slowness vector at the location over the shape which provides additional visualization of the EP activity. In general, the conduction arrows have different lengths that represent the magnitude of the slowness in addition to its direction.

In FIG. 2, an ellipsoid 202 intersects with the anatomical surface to define a curved surface area (e.g., region) 205 having a boundary 207 on the EP map surface. It can be seen that, within area 205, some of conduction arrows 220 seem to share a common origin. However, since this visual perception may be misleading, a quantitative analysis, such as disclosed below, is required to verify the presence of a focal source of arrhythmia inside region 205 (e.g., in a location 204). The analysis may indeed find a respective set of origin vectors that is included in the set of conduction arrows 220 and that they are the result of a focal source.

To this end, after identifying region 205 as potentially including a source using directed graphs, as described in FIG. 3, a processor can estimate if the sign of one of the following divergence theorem integrals is positive, in order to determine if a source is indeed present therein:

$$\iint (\nabla \cdot V_s) dr \quad \oint (V_s \cdot \hat{n}) dl$$

The left integral is a surface integral over region 205, while the right-side integral is a line integral over a boundary 1 207 of region 205. $V_s$ is a 2D vector function approximation of the velocity origin vectors, which is defined over the curved surface (i.e., 2D manifold) 295.

In addition, the disclosed technique estimates where the inside region 205 is an exact location 204 of a source (for example by finding an average location).

Alternatively, a processor can estimate if the sign of one of the following divergence theorem integrals is positive, in order to determine if a source is present:

$$\iiint (\nabla \cdot V) dr \quad \oiint (V \cdot \hat{n}) dS$$

The left integral is a volume integral over ellipsoid 202, while the right-side integral is a surface integral over surface S of the ellipsoid 202. V is a vector function approximation of the velocity origin vectors, which is defined over the volume of ellipsoid 202.

Figures 3A, 3B:
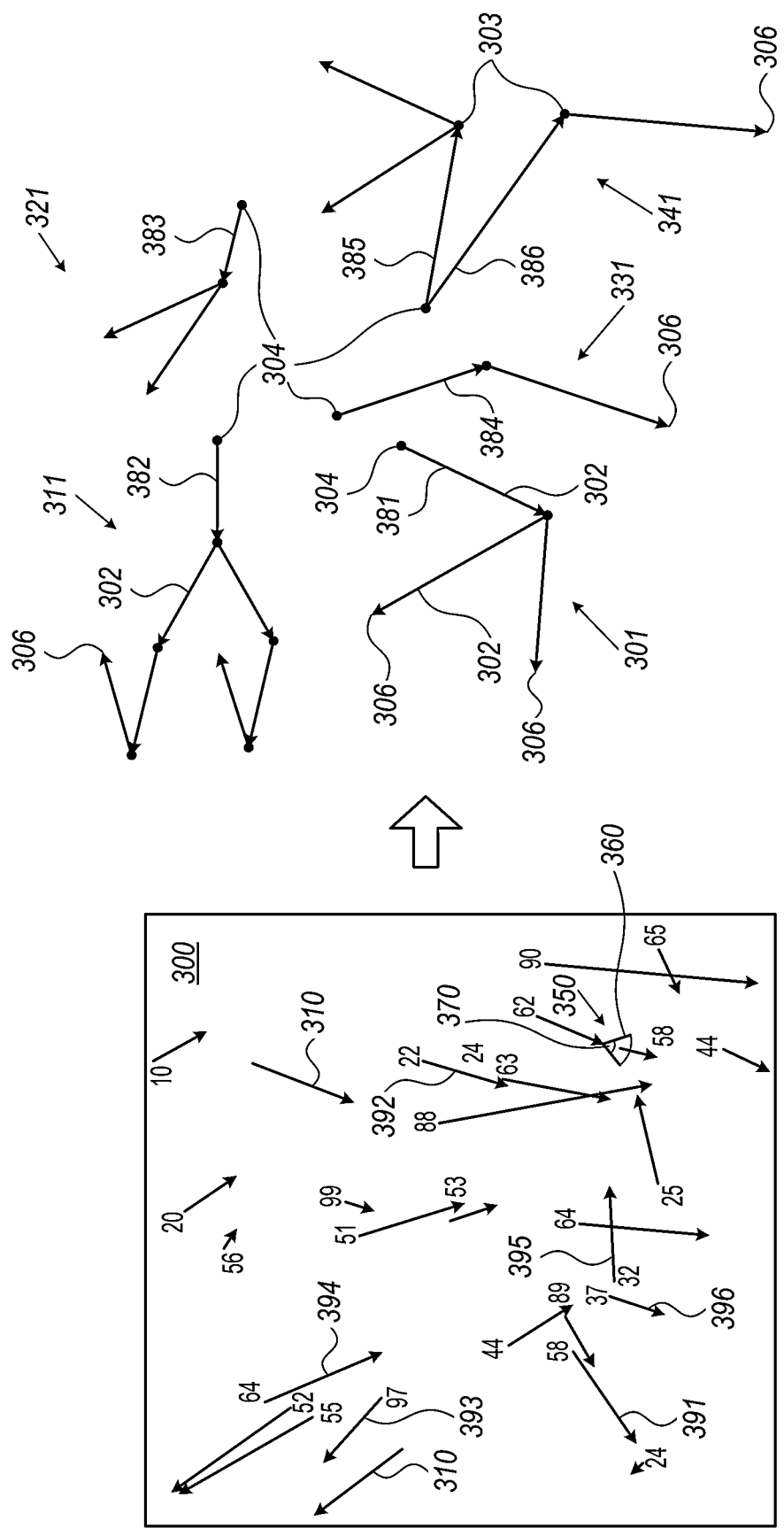
FIGS. 3A and 3B are schematic drawings of a set of velocity vectors and of a set of directed graphs based on the velocity vectors, respectively, in accordance with an example of the present disclosure.

FIGS. 3A and 3B are schematic drawings of a set 300 of velocity vectors 310 and of a set of directed graphs 301, 311, 321, 331 and 341 that are based on velocity vector set 300, in accordance with an example of the present disclosure. The set of velocity vectors 300 is taken from a continuous portion (e.g., region) of an EP map surface comprising velocity vector map 200. Proper mathematical methods exist to transform (e.g., project) the vectors between a curved surface (such as in map 200) and a 2D plot (such as in FIG. 3A), or a 3D plot (not shown), the latter used in a natural way to represent the vectors lying on a variably curved surface in 3D.

FIG. 3A shows a set 300 of velocity vectors 310 that cover a portion of the anatomical surface. The simplified figure for clarity of presentation is 2D while in practice the vectors are in 3D.

Processor 28 has numbered the vectors so as to have the vectors indexed for arranging in directed graphs. By numbering (e.g., giving an index) to the vectors, the processor ensures all vectors are considered in the process of generating from these a unique set of directed graphs.

Processor 28 mays number the vectors, for example, based on local activation time (LAT) values at respective tail locations, so as to have the vectors ready for arranging in directed graphs. The same LAT values, up to a given tolerance, at two sufficiently close (e.g., within few mm tolerance) vector locations indicate that the two vectors can be considered as sharing a common tail.

As described later in FIG. 3B, using directed graphs, the processor will identify vectors 391, 392, 393, 394, 395 and 396 as origin vectors.

To generate a direct graph from vectors 310, the processor uses a newly disclosed method in which each the processor generates and assigns to (e.g., aligns with) each vector head a cone (shown in 2D as angular section 350) with predefined radius 360 and a given solid angle (shown in 2D as angle 370). If a tail of another vector falls within the cone, the processor generates from the two vectors a directed graph portion. The processor goes over all vectors, and deletes overlapping selectins (e.g., reoccurring directed graph portions), until a unique full set of directed graphs is received. Isolated vectors, e.g., that were not associated using the disclosed method with any other vectors are also considered (minimal) directed graphs.

FIG. 3B shows schematically directed graphs 301, 311, 321, 331 and 341 that are based on some of the velocity vectors 310 of set 300. As seen, each of these directed is made of arcs 302 and vertices 303, and has a unique origin vertex 304. Open ends 306 of arcs count the outdegree of each directed graph. For example, directed graph 321 has an indegree=1 and an outdegree=2.

The processor strips each directed graph from its branches, which leaves only a set of "stripped" directed graphs, that are all origin arcs.

At this stage the processor considers only origin vectors that correspond to the origin arcs found. By way of example, origin locations 304 of arcs 381, 382, 383, 384, 385 and 386, of the directed graphs correspond respectively to origin vectors 391, 392, 393, 394, 395 and 396. Some of the origin vectors fall within area 205 of FIG. 2 that the processor defined and are therefore considered to be in close proximity to one another.

The processor now tests with a calculus analysis described above if the origin vectors of area 205 are indicative of an arrhythmogenic focal source.

In some examples, using a predefined criterion (e.g., minimal number of such vectors at each given volume), the processor fits a vector field function to the vectors (e.g., fits velocity vector field approximation function V(r)), and applies the divergence theorem to V(r). In other examples the processor may consider the discrete set of origin vectors and calculate a discrete version of the divergence.

If the answer is yes (i.e., positive divergence), the processor calculates the average of locations 304 and indicates that location (e.g., a projected location from the space of the directed graphs onto the anatomical surface) on the EP map as an arrhythmogenic focal source.

Figure 4:
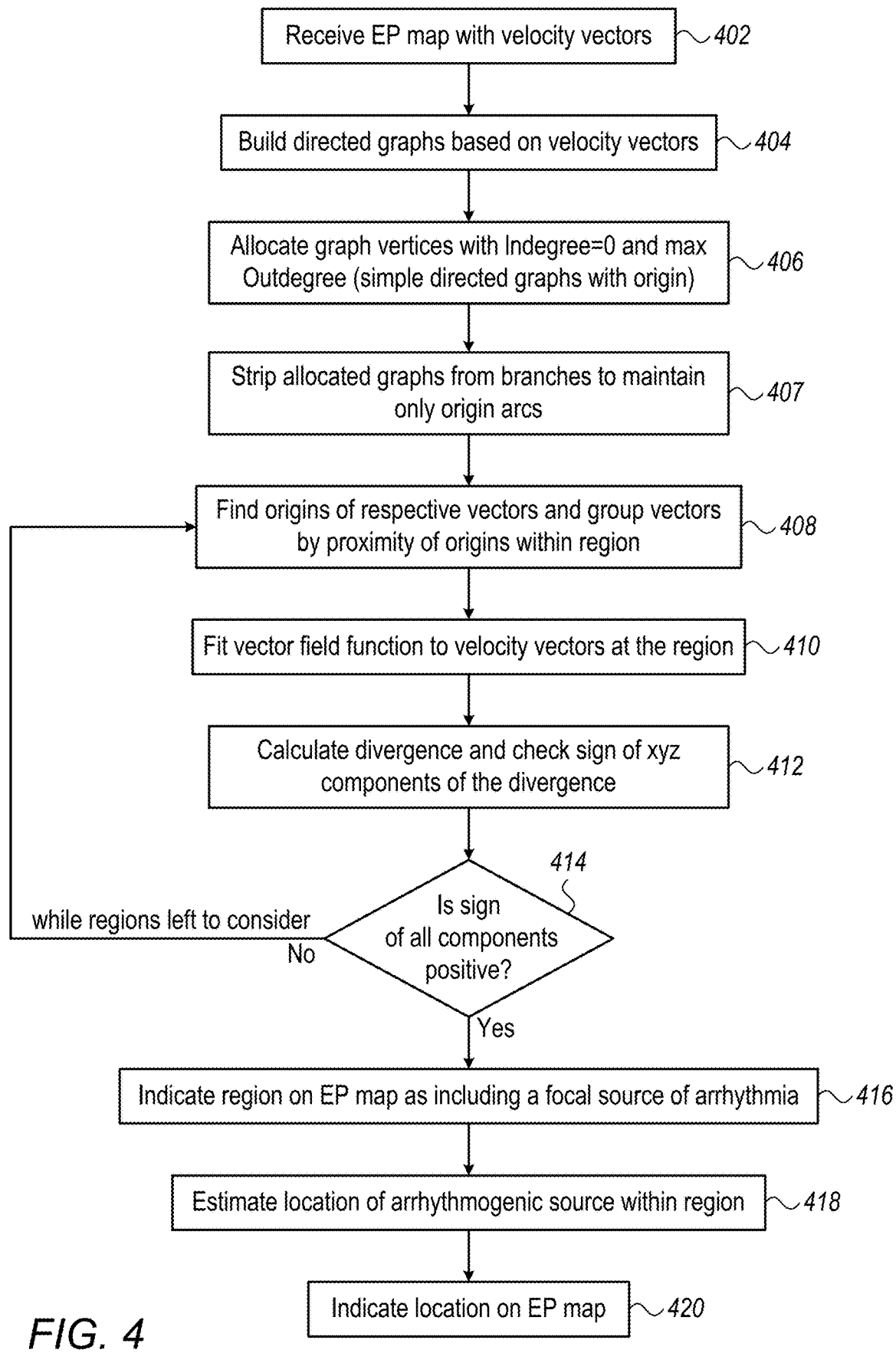
FIG. 4 is a flow chart that schematically illustrates a method for identifying a focal source of an arrhythmia, in accordance with an example of the present disclosure.

FIG. 4 is a flow chart that schematically illustrates a method for identifying a focal source of an arrhythmia, in accordance with an example of the present disclosure. The algorithm, according to the presented example, carries out a process that begins with processor 28 receiving (e.g., uploading) an EP map comprising velocity vectors, such as EP map 200 of FIG. 2, at a map of velocity vectors uploading step 402.

Next, based on the velocity vectors, the processor builds a set of directed graphs, at directed graphs building step 404. An example of this step is seen in FIGS. 3A and 3B.

At directed graphs allocation step 406, the processor selects those simple directed graphs that have an origin and which have the most open-ended arcs, e.g., having a maximal outdegree value. In another example, the processor selects a subset of directed graphs, also with an origin, that may also include more complex (e.g., multi vertex graphs) and that are most unbalanced in favor of open-ended arcs.

At a directed graph stripping step 407, the processor strips the branches from the direct graphs and maintains only origin arcs of the graphs.

In step 408 of grouping directed graphs, processor 28 finds tail locations of respective origin vectors and groups which are in spatial proximity to one another, such as within a surface area (e.g., area 205).

At a vector field function fitting step 410, the processor fits a velocity vector field approximation function V(r) to the origin vectors in the region (e.g., in manifold region 205).

Using the divergence theorem, the processor calculates if the origin vectors all point away from a focal source at a focal source determination step 412. For example, if the vector derivative along each of the x, y, z axis is greater than 0, ∇·V>0, then the origin vectors are all pointing away from a focal source.

If the answer in a checking step 414 is "no," the process returns to step 408, to search for a focal source in another region of the velocity vectors map.

If the answer checking step 414 is "yes," the processor indicates the checked region on the EP map as including a focal source of arrhythmia, at arrhythmogenic region indication step 416.

In a subsequent, optional step of indication of arrhythmogenic location step 418, the processor calculates an average location based upon tail locations of all vectors. Finally, the processor graphically indicates the identified cardiac tissue location on the EP map, e.g., a tissue area for a user to consider for ablation.

Finally, at an arrhythmogenic location displaying step 20, the processor displays the location found in step 418 on the EP map.

EXAMPLES

Example 1

A system (10) includes a display (27) and a processor (56). The processor is configured to (i) receive a cardiac electrophysiological (EP) velocity vectors (220) map (200), (ii) compute a set of directed graphs (301, 311, 321, 331, 341) from at least some of the velocity vectors (220), (iii) using the directed graphs (301, 311, 321, 331, 341), identify respective origin velocity vectors (391, 392, 393, 394, 395, 396) on the EP velocity vectors map (200), (iv) define one or more regions (205) on the EP velocity vectors map, (v) determining, based on origin velocity vectors in each of the one or more regions, whether the one or more regions (205) contain a focal source (204) of an arrhythmia, and (vi) visualize regions (205) identified to contain a focal source (204) on the EP map (200) to a user, on the display (27).

Example 2

The system according to example 1, wherein the processor (56) is further configured to estimate a location (204) of the focal source inside the region (205) and visualize the location (204) on the EP map (200).

Example 3

The system according to any of examples 1 and 2, wherein the processor (56) is configured to compute the set of directed graphs (301, 311, 321, 331, 341) by arranging the velocity vectors (220) according to spatial and temporal proximity among the velocity vectors.

Example 4

The system according to any of examples 1 through 3, wherein first and second velocity vectors (220) are considered spatially and temporally proximate if (i) tail locations of the first and second velocity vectors share a same local activation time (LAT) up to a threshold tolerance, and (ii) the tail locations are separated by no more than a threshold distance.

Example 5

The system according to any of examples 1 through 4, wherein the processor (56) is configured to identify the region (205) by determining three or more origin vectors being within a predefined spatial proximity to one another.

Example 6

The system according to any of examples 1 through 5, wherein the processor (56) is configured to ascertain whether the region (205) contains the focal source (204), by fitting a vectorial function to velocity origin vectors in the region and performing a vector calculus operation on the fitted vectorial function.

Example 7

The system according to any of examples 1 through 6, wherein the processor (56) is configured to ascertain whether the region (205) contains the focal source (204) by estimating whether a sign of a divergence of the fitted vectorial function in the region is positive.

Example 8

The system according to any of examples 1 through 7, wherein the processor (56) is configured to compute a set of directed graphs (301, 311, 321, 331, 341) from at least some of the velocity vectors (220) by performing the steps comprising of (i) assigning to each velocity vector (220) head a cone (250) with predefined radius (260) and a given solid angle (270), and (ii) if a tail of another vector (220) falls within the cone, the, generating from the two vectors a directed graph (301, 311, 321, 331, 341) portion.

Example 9

The system according to any of examples 1 through 8, wherein the processor (56) is configured to, using the directed graphs, identify respective origin velocity vectors (391, 392, 393, 394, 395, 396), by identifying origin arcs (381, 382, 383, 384, 385, 386) and matching to each origin arc an origin vector.

Example 10

A method includes receiving a cardiac electrophysiological (EP) velocity vectors (220) map (200). A set of directed graphs (301, 311, 321, 331, 341) is computed from at least some of the velocity vectors (220). Using the directed graphs (301, 311, 321, 331, 341), respective origin velocity vectors (391, 392, 393, 394, 395, 396) are identified on the EP velocity vectors map (200). Determining, based on origin velocity vectors in each of the one or more regions, whether one or more regions (205) are checked if containing a focal source (204) of an arrhythmia. Regions (205) identified to contain a focal source (204) are visualized on the EP map (200) to a user, on the display (27).

It will be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for identifying a focal source of a cardiac arrhythmia in a patient during an electrophysiological (EP) procedure, comprising:
   a display;
   one or more intracardiac electrodes configured to be positioned within a heart chamber of the patient; and
   one or more processors that are communicatively coupled to the display and to the one or more intracardiac electrodes positioned within a heart chamber of the patient, wherein the one or more processors are collectively configured to:
   generate a cardiac EP velocity vectors map based on signals acquired by the one or more intracardiac electrodes, wherein the EP velocity vectors map includes a plurality of velocity vectors;
   compute a set of directed graphs from at least some of the plurality of velocity vectors, wherein the directed graphs are computed, for each respective velocity vector in the plurality of velocity vectors, by defining a cone originating at a head of the respective velocity vector and generating a graph connection only when a tail of another velocity vector falls within the cone;
   using the directed graphs, identify origin velocity vectors on the EP velocity vectors map;
   define one or more regions on the EP velocity vectors map;
   determine, based on respective origin velocity vectors that are located in each of the one or more regions, whether the one or more regions contain the focal source of the arrhythmia, wherein respective origin velocity vectors are among the origin velocity vectors; and
   display, during the EP procedure, the EP velocity vectors map and regions identified to contain the focal source on the EP velocity vectors map on the display.

2. The system according to claim 1, wherein the one or more processors are further collectively configured to;
   estimate a location of the focal source inside the regions and visualize the location on the EP velocity vectors map.

3. The system according to claim 1, wherein the one or more processors are collectively configured to;
   compute the set of the directed graphs by arranging the plurality of the velocity vectors according to spatial and temporal proximity among the plurality of the velocity vectors.

4. The system according to claim 3, wherein the one or more processors are further collectively configured to:
   select a first velocity vector and a second velocity vector from among the plurality of the velocity vectors, and
   determine whether the first velocity vector and the second velocity vector are spatially and temporally proximate based on if (i) tail locations of the first and second velocity vectors share a same local activation time (LAT) up to a threshold tolerance, and (ii) the tail locations are separated by no more than a threshold distance.

5. The system according to claim 1, wherein the one or more processors are further collectively configured to:
   identify the regions by determining three or more origin vectors among the origin velocity vectors that are located within a predefined spatial proximity to one another.

6. The system according to claim 1, wherein the one or more processors are further collectively configured to;
   ascertain whether the regions contain the focal source, by fitting a vectorial function to the respective velocity origin vectors in the regions to form a fitted vectorial function, and
   perform a vector calculus operation on the fitted vectorial function.

7. The system according to claim 6, wherein the one or more processors are configured to:
   ascertain whether the region contains the focal source by estimating whether a sign of a divergence of the fitted vectorial function in the region is positive.

8. The system according to claim 1, wherein the one or more processors are further collectively configured to:
   using the directed graphs, identify the origin velocity vectors, by identifying respective origin arcs and matching to each respective origin arc an associated origin vector.

9. A method for identifying a focal source of arrhythmia in a patient during a electrophysiological (EP) procedure, the method comprising:
   acquiring electrical signals by a plurality of intracardiac electrodes positioned within a heart chamber of the patient;
   generating EP velocity vectors map based on the electrical signals acquired by the plurality of intracardiac electrodes positioned within a heart chamber of the patient, wherein the EP velocity vectors map includes a plurality of velocity vectors;
   computing a set of directed graphs from at least some of the plurality of velocity vectors, wherein the directed graphs are computed, for each respective velocity vector in the plurality of velocity vectors, by defining a cone originating at a head of the respective velocity vector and generating a graph connection only when a tail of another velocity vector falls within the cone;
   using the directed graphs, identifying origin velocity vectors on the EP velocity vectors map;
   defining one or more regions on the EP velocity vectors map;
   determining, based on respective origin velocity vectors that are located in each of the one or more regions, whether the one or more regions contain the focal source of an arrhythmia, wherein respective origin velocity vectors are among the origin velocity vectors; and
   displaying, during the EP procedure, the EP velocity vectors map and regions identified to contain the focal source on the EP velocity vectors map for guiding ablation treatment of the patient.

10. The method according to claim 9, further comprising:
    estimating a location of the focal source inside the regions, and
    visualizing the location on the EP velocity vectors map.

11. The method according to claim 9, wherein computing the set of the directed graphs comprises arranging the plurality of the velocity vectors according to spatial and temporal proximity among the plurality of the velocity vectors.

12. The method according to claim 11, further comprising:
    selecting a first velocity vector and a second velocity vector from among the plurality of the velocity vectors;
    determining whether the first velocity vector and the second velocity vector are spatially and temporally proximate based on if (i) tail locations of the first and second velocity vectors share a same local activation time (LAT) up to a threshold tolerance, and (ii) the tail locations are separated by no more than a threshold distance.

13. The method according to claim 11, wherein the identifying comprises determining three or more origin vectors among the origin velocity vectors that are located within a predefined spatial proximity to one another.

14. The method according to claim 11, further comprising:
    fitting a vectorial function to the respective velocity origin vectors in the regions to form a fitted vectorial function, and
    performing a vector calculus operation on the fitted vectorial function.

15. The method according to claim 14, further comprising:
    estimating whether a sign of a divergence of the fitted vectorial function in the region is positive.

16. The method according to claim 9, wherein the identifying comprises;
    identifying respective origin arcs and matching to each respective origin arc an associated origin vector.

17. A non-transitory computer readable storage medium storing instruction for identifying a focal source of arrhythmia in a patient during a electrophysiological (EP) procedure, the instructions when executed by a processor of a console cause the console to perform a method comprising:
    acquiring electrical signals by a plurality of intracardiac electrodes positioned within a heart chamber of the patient;
    generating EP velocity vectors map based on the electrical signals acquired by the plurality of intracardiac electrodes positioned within a heart chamber of the patient, wherein the EP velocity vectors map includes a plurality of velocity vectors;
    computing a set of directed graphs from at least some of the plurality of velocity vectors, wherein the directed graphs are computed, for each respective velocity vector in the plurality of velocity vectors, by defining a cone originating at a head of the respective velocity vector and generating a graph connection only when a tail of another velocity vector falls within the cone;
    using the directed graphs, identifying origin velocity vectors on the EP velocity vectors map;
    defining one or more regions on the EP velocity vectors map;
    determining, based on respective origin velocity vectors that are located in each of the one or more regions, whether the one or more regions contain the focal source of an arrhythmia, wherein respective origin velocity vectors are among the origin velocity vectors; and
    displaying, during the EP procedure, the EP velocity vectors map and regions identified to contain the focal source on the EP velocity vectors map for guiding ablation treatment of the patient.

\* \* \* \* \*